United States Patent [19]
Gandhi et al.

[11] Patent Number: 5,608,048
[45] Date of Patent: Mar. 4, 1997

[54] $d_4T$ POLYMORPHIC FORM 1 PROCESS

[75] Inventors: Rajesh B. Gandhi, Liverpool; Joseph B. Bogardus, Manlius; Peter M. Garofalo, Syracuse; Timothy R. Marr, Deruyter; Robert K. Perrone, Liverpool; Murray A. Kaplan, Syracuse, all of N.Y.

[73] Assignee: Bristol-Myers Squibb Company, Princeton, N.J.

[21] Appl. No.: 465,208

[22] Filed: Jun. 5, 1995

[51] Int. Cl.$^6$ .................................................. C07H 19/06
[52] U.S. Cl. ........................................ 536/28.2; 536/27.14
[58] Field of Search .............................. 536/27.14, 28.2, 536/55.3; 514/49, 50

[56] References Cited

U.S. PATENT DOCUMENTS 4,476,248 10/1984 Gordon et al. ......................... 536/28.2
4,904,770 2/1990 Starrett, Jr. et al. .................. 536/27.14
4,978,655 12/1990 Lin et al. ................................ 536/28.2

OTHER PUBLICATIONS

Udupa, N, "Effect of Crystallinity and Solubilizing Agents on Absorption and Excretion Patterns of Ibuprofen," The Eastern Pharmacist, Scientific Section, vol. XXX, No. 350, pp. 137–140 (Feb. 1987).
Harte, W. E., et al., *Biochemical and Biophysical Research Comm.*, 175(1), pp. 298–304 (1991).
Gurskaya, G. V., et al., Molekulyarnaya Biologiya, 25(2), pp. 483–491 (Mar.–Apr., 1991) (Russian) translated 1991 in Plenum Publishing Corp., pp. 401–408.

*Primary Examiner*—James O. Wilson
*Attorney, Agent, or Firm*—Samuel J. DuBoff

[57] ABSTRACT

The present invention concerns a novel process using controlled cooling for obtaining $d_4T$ polymorphic Form I from a mixture containing one or more of polymorphic Forms I, II and III. Compound $d_4T$ has been approved for use in the treatment of AIDS.

5 Claims, No Drawings

$d_4T$ POLYMORPHIC FORM 1 PROCESS

BACKGROUND OF THE INVENTION

1. Field of the Invention

The present invention concerns a process for obtaining $d_4T$ polymorphic Form I from a mixture containing one or more of polymorphic Forms I, II and III.

2. Background Art

The compound $d_4T$ (2',3'-didehydro-3'-deoxythymidine) has been approved for use in the treatment of AIDS. The drug has been named Stavudine by the USAN and is marketed as Zerit®. The structure is as follows:

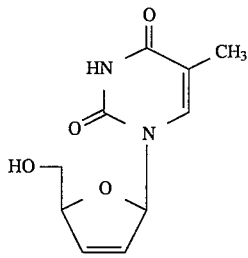

The synthesis of this compound and its biological properties are described in T. S. Lin, et. al. U.S. Pat. No. 4,978,655 granted Dec. 18, 1990.

Other processes for making $d_4T$ have been reported in the literature such as in Starrett, Jr. et. al. U.S. Pat. No. 4,904,770 granted Feb. 27, 1990.

In the course of preparing larger batch lots of $d_4T$ for clinical testing, a problem was experienced in that the solubility of the compound was found to vary significantly from lot to lot. Since differences in solubility are consistent with different polymorphic forms, further investigation verified the existence of three solid state forms of $d_4T$, designated as Forms I, II, and III. Forms I and II are anhydrous polymorphs, whereas Form III is hydrated [$(d_4T)_3 \cdot H_2O$] and is pseudopolymorphic with Forms I and II. Solid state transformation studies were performed under various stress conditions of moisture, heat, and vacuum. Form I is stable and shows no transformation to other polymorphic forms, thus demonstrating its greater thermodynamic stability relative to the other forms. However, Form III converted to Form I only when heated for 24 hours under vacuum at 80° C.

The capacity to occur in different crystal structures is known as polymorphism and is known to occur in many organic compounds including drugs. These different crystalline forms are known as "polymorphic modifications" or "polymorphs" and are realized only in the crystalline state. While polymorphic modifications have the same chemical composition, they differ in packing, geometrical arrangement, and other descriptive properties of the crystalline solid state. As such, these modifications may have different solid-state physical properties such as shape, color, density, hardness, deformability, stability, dissolution properties, and the like. Polymorphism of an organic drug molecule and its consequences would be appreciated by one skilled in the pharmaceutical arts. As an example; Gordon, et. al. in U.S. Pat. No. 4,476,248, issued Oct. 7, 1984, disclosed and claimed a new crystalline form of the drug ibuprofen as well as the process for producing it. The new crystalline form was reported to improve the manufacturability of ibuprofen.

The issue of polymorphism is a well understood and critical aspect in the drug development process. In order to produce a solid state dosage form with predictable efficacy, dissolution properties, and stability (bulk and dosage stages), it is necessary to determine the existence of any solid state forms of the material and their respective solid state stability, dissolution, and thermodynamic properties. Subsequently, the proper form may be selected for development. All of these factors were considered in the development of $d_4T$.

Since Form I has been found to be the most thermodynamically stable form, with no tendency for solid state conversion to Form II or III, this is the form sold commercially as Zerit®.

It is therefore an object of this invention to be able to reliably, conveniently and reproducibly prepare $d_4T$ Form I.

SUMMARY OF THE INVENTION

The present invention relates to a process for preparing $d_4T$ polymorphic Form I from a mixture containing one or more of $d_4T$ polymorphic Forms I, II and III which comprises:

(a) dissolving the mixture under anhydrous conditions in an organic solvent to form a saturated solution at a temperature of at least about 65° C., wherein said solvent is selected from the group consisting of methanol, ethanol, n-propanol, isopropanol, acetonitrile and ethyl acetate;

(b) continuously stirring while cooling the solution until the precipitation of substantially pure crystalline $d_4T$ polymorphic Form I is substantially complete, provided the cooling rate does not exceed about 20° C. per hour until a solution temperature of about 40° C. is reached, and (c) recovering substantially pure crystalline $d_4T$ polymorphic Form I.

A preferred embodiment is the process wherein step (a) further comprises adding seed crystal of $d_4T$ polymorphic Form I to the solution.

Another preferred embodiment is the process wherein the solvent is isopropanol.

Another preferred embodiment is the process wherein the cooling in step (b) comprises reducing the solution temperature about 10° C. in 15 minutes, holding the solution at the resulting temperature for about one hour, repeating this procedure until a solution temperature of about 40° C. is reached, and further reducing the solution temperature until the precipitation of substantially pure crystalline $d_4T$ polymorphic Form I is substantially complete.

Another preferred embodiment is the process wherein the cooling in step (b) comprises reducing the solution temperature from 75°–82° C. to 65°–75° C. in about 30 minutes to one hour, further reducing the temperature to about 40°–45° C. during an additional 2 to 3 hours, and then rapidly reducing the temperature to about –5° C. to 5° C.

DETAILED DESCRIPTION OF THE INVENTION

In marketing $d_4T$ on a large scale for preparing commercial product, it has been found that variations existed in the solubility from lot to lot which were attributable to the presence of one or more of polymorphic $d_4T$ Forms I, II and III.

This problem was not heretofore recognized nor alleviated by routine manufacturing or purification procedures.

Early drug substance characterization studies showed slight solubility differences for $d_4T$ obtained from different lots, sources, and recrystallization processes. Powder X-ray diffraction patterns were also found to be different. Further investigation supported the existence of three distinct polymorphic Forms I, II, and III, and preliminary methods were identified to prepare each form. Initially, Form I was isolated by slow cooling of warm, highly concentrated aqueous solutions of $d_4T$. Subsequently, it was learned that Form II could be prepared by rapid cooling of hot, concentrated solutions of $d_4T$ in solvents such as ethanol or isopropanol. This type of crystallization, however, sometimes produced mixtures of Forms I and II. Form III, a hydrate, was initially isolated by addition of hydrochloric acid to a concentrated alkaline solution of $d_4T$ in water.

Forms I, II and III can best be distinguished by their characteristic X-ray powder diffraction patterns indicating diffraction angles (i.e. degrees 2Θ) and relative intensities (i.e. % $I/I_o$) provided in Table 1 below.

TABLE 1

Diffraction Angles and Relative Intensities Measured in the Powder X-ray Diffraction Patterns of Stavudine

| Peak Number | (Form I) degrees 2Θ | % $I/I_o$ | (Form II) degrees 2Θ | % $I/I_o$ | (Form III) degrees 2Θ | % $I/I_o$ |
|---|---|---|---|---|---|---|
| 1 | 9.12 | 100 | 9.24 | 100 | 6.51 | 24 |
| 2 | 10.87 | 51 | 11.24 | 34 | 7.33 | 10 |
| 3 | 17.16 | 13 | 16.47 | 5 | 9.10 | 100 |
| 4 | 17.72 | 6 | 17.03 | 1 | 10.79 | 26 |
| 5 | 18.31 | 23 | 18.60 | 84 | 11.40 | 30 |
| 6 | 19.14 | 48 | 20.19 | 6 | 12.27 | 19 |
| 7 | 21.88 | 12 | 22.63 | 6 | 13.06 | 35 |
| 8 | 22.32 | 6 | 22.95 | 30 | 15.45 | 98 |
| 9 | 22.85 | 11 | 24.28 | 7 | 16.67 | 9 |
| 10 | 23.27 | 30 | 25.54 | 4 | 17.12 | 15 |
| 11 | 23.78 | 14 | 26.51 | 17 | 17.86 | 6 |
| 12 | 24.62 | 21 | 27.11 | 20 | 18.30 | 13 |
| 13 | 25.26 | 2 | 28.06 | 8 | 21.44 | 27 |
| 14 | 26.15 | 12 | 29.36 | 2 | 22.06 | 14 |
| 15 | 27.37 | 10 | 30.13 | 2 | 22.85 | 86 |
| 16 | 28.56 | 14 | 31.08 | 2 | 23.97 | 5 |
| 17 | 28.94 | 9 | 31.59 | 5 | 24.43 | 16 |
| 18 | 29.92 | 7 | 34.27 | 2 | 25.01 | 15 |
| 19 | 34.97 | 7 | 36.76 | 3 | 26.76 | 8 |
| 20 | 35.62 | 3 | 37.54 | 1 | 27.33 | 6 |
| 21 | 37.19 | 2 | 37.92 | 2 | 27.92 | 18 |
| 22 | 39.74 | 3 | — | — | 28.67 | 5 |
| 23 | — | — | — | — | 29.50 | 8 |
| 24 | — | — | — | — | 30.97 | 4 |
| 25 | — | — | — | — | 33.88 | 10 |
| 26 | — | — | — | — | 39.71 | 3 |

The characteristic diffraction angles 2Θ that distinguish any form from a mixture are 19.1° for Form I; 11.2° and 18.6° for Form II; and 6.5°, 7.3°, and 15.5° for Form III.

Such data in Table 1 was obtained by packing a sample specimen onto a glass slide with a 0.2 mm sample well, which was analyzed using a Rigaku Geigerflex powder diffractometer with a copper target X-ray tube and a nickel filter. The sample was scanned from 5° to 40° 2Θ. The resulting powder pattern was used to prepare a table of peak diffraction angle (2Θ) vs. peak intensity ratio ($I/I_o$) for each diffraction line observed.

Additionally, single crystal X-ray analysis according to the procedure described in Harte, W. E., et. al., *Biochemical and Biophysical Research Comm.*, 175(1), pp. 298–304 (1991) have resulted in the following crystallographic data for Forms I, II and III presented in Table 2 below.

TABLE 2

| Form | a | b | c | α° | β° |
|---|---|---|---|---|---|
| 1 | 11.662(1) | 5.422(1) | 16.233(3) | 90 | 92.64(1) |
| 2 | 5.493(1) | 9.881(1) | 10.077(1) | 105.04(1) | 102.34(1) |
| 3 | 16.299(2) | 23.948(7) | 5.582(1) | 90 | 90 |

| Form | δ° | Space Group (S.G.) | Volume of Cell (V cell) | No. of Molecules (Z) | Calculated Density ($D_{calc}$) |
|---|---|---|---|---|---|
| 1 | 90 | $P2_1$ | 1025.4(5) | 4 | 1.452 |
| 2 | 89.61(1) | P1 | 515.3(2) | 2 | 1.445 |
| 3 | 90 | $P2_12_12_1$ | 2179(1) | 8 | 1.394 |

This data is in agreement with that presented in the Harte publication for Form I, as well as the data presented for Form II in Gurskaya, G. V., et. al., *Molekulyarnaya Biologiya*, 25(2), pp. 483–91 (1991) (Russian), translated 1991 in Plenum Publishing Corp., pp. 401–08.

A typical reaction scheme for making $d_4T$ on a large scale is shown in Scheme A below:

Scheme A

1. Thymidine to $d_4T$-I

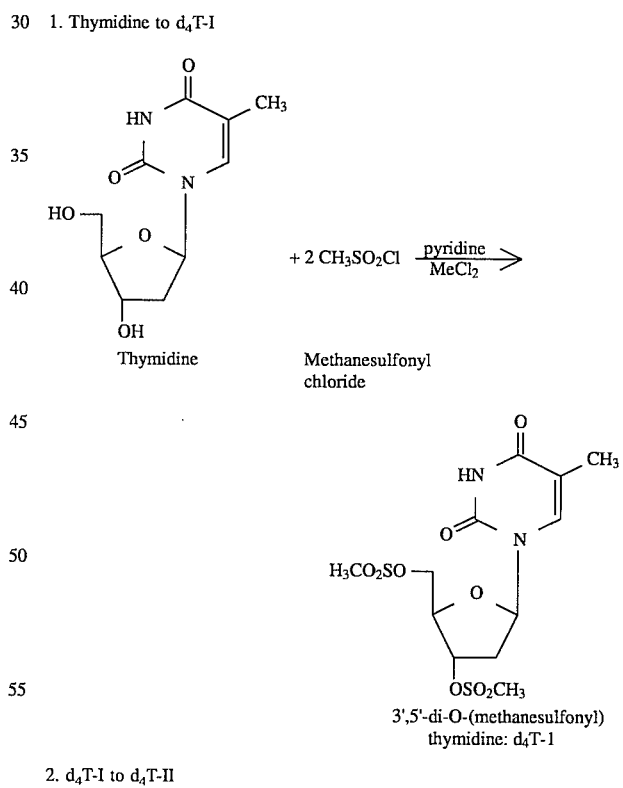

2. $d_4T$-I to $d_4T$-II

-continued
Scheme A

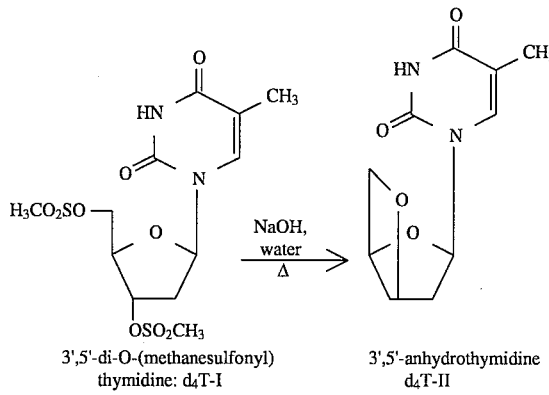

3',5'-di-O-(methanesulfonyl) thymidine: d₄T-I 3. d₄T-II to d₄T Crude Part I

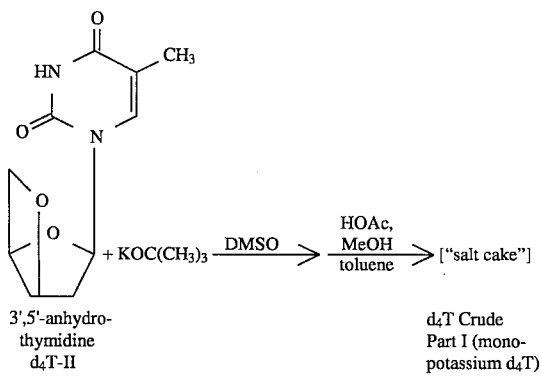

4. d₄T Crude Part I to d₄T-Primary

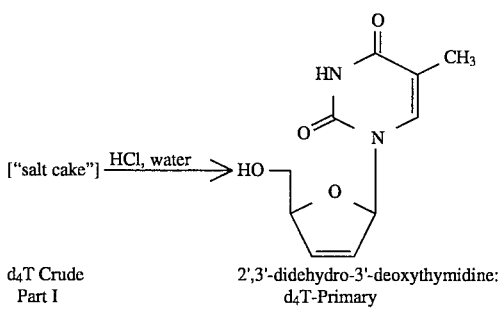

5. d₄T-Primary to d₄T-RX (no structural change takes place)

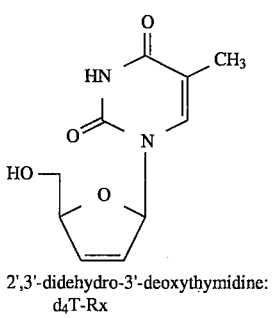

2',3'-didehydro-3'-deoxythymidine: d₄T-Rx 6. d₄T-Primary (and/or d₄T-Rx) to d₄T-FP (no structural change takes place)

-continued
Scheme A

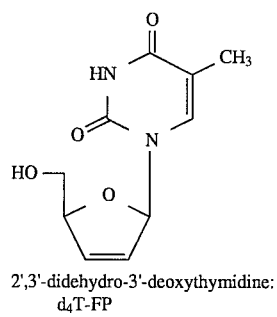

2',3'-didehydro-3'-deoxythymidine: d₄T-FP

Stage I—Conversion of Thymidine to d₄T-I

Thymidine (35.0 kgW, 144.5 moles) is slurried in methylene chloride (105 L). Pyridine (45.9 kgW, 580.3 moles) is added to the slurry, followed by a rinse of methylene chloride (8.8 L) while maintaining the slurry temperature at 20° to 35° C. Methanesulfonyl chloride (48.3 kgW, 421.6 moles) is diluted with methylene chloride (4.6 L). The solution is added to the slurry at 20° to 30° C.; this is followed by a rinse of methylene chloride (22.1 L). The resulting solution is held for approximately 10 to 20 hours at 20° to 35° C. A precipitate forms during the holding period. Upon completion of the holding period, water (4.6 L) is added to the reaction mixture. Then, the batch temperature is adjusted to approximately 30° C. Water (595 L) is added into a separate vessel, and the temperature is adjusted to approximately 25° C. The reaction mixture is added to the water over approximately 15 minutes, maintaining the temperature at 23° to 35° C., then it is rinsed with water. The resulting slurry is agitated, and the pH of the slurry is adjusted to 2.5 to 2.7 by adding 12N hydrochloric acid (approximately 3.0 L). The slurry temperature is adjusted to approximately 25° C., and the mixture is agitated for approximately two hours. The product slurry is filtered and washed first with water, then with methylene chloride, and finally with water. The filter is blown with warm nitrogen for approximately four hours. The wet product cake is then dried in an air oven at 45° C. to 50° C. to an LOD (i.e., loss on drying) of <1%. Approximately 50–53 kgW (i.e., 87–92% of theoretical yield) of d₄T-I are obtained.

Stage II—Conversion of d₄T-I to d₄T-II

An initial portion of d₄T-I (27.0 kgW, 67.8 moles) is dissolved in a water (63 L, approximately 35° C.) and 30% sodium hydroxide (20.7 L) solution and held with agitation at 30° to 35° C. for approximately ten minutes. Subsequently, ten aliquots of d₄T-I (6.3 kgW each; 63 kgW [158.1 moles] total) and 30% w/w sodium hydroxide solution (4.8 L each; 48 L [478.8 moles] total) are added to the reaction mix at 30° to 35° C. with approximately ten-minute holding times between aliquot additions. The reaction mixture is warmed to 68° to 72° C., then held for approximately one hour. The reaction is monitored for completeness by HPLC analysis. After the reaction is completed, the batch is cooled to 10° to 15° C. Crystallization is induced by the addition of portions (1 L each) of 12N hydrochloric acid (approximately 9 L total) to a pH of 9.6 to 10.0. When crystallization begins, acid addition is halted and the slurry is stirred for approximately 15 minutes. The pH adjustment is then continued to a final pH of 6.0 to 6.5. The resulting slurry is cooled to 0° to 5° C. and held within this temperature range for approximately two hours. The slurry is filtered, then washed with 0° to 5° C. water. The wet product is dried at 45° to 50° C. in an air oven to an LOD of <0.5%. The resultant dry product yield is 36 to 38 kgW of $d_4$T-II (i.e., 71–75% of theory).

Stage III—Conversion of $d_4$T-II to $d_4$T Primary $d_4$T-II (15.0 kgW, 66.9 moles) is dissolved in dimethyl sulfoxide (60 L) and then cooled to approximately 18° C. Solid potassium tertiarybutoxide is added to the solution in five aliquots (3 kgW each; 15 kgW [133.8 moles] total) while the batch temperature is maintained at 18° to 30° C. The addition of each aliquot is followed by a brief holding period. The total addition time is approximately 90 minutes. Glacial acetic acid (1.92 L, 33.5 moles) is added portionwise to the batch over 1 to 2 hours, maintaining the temperature between 25° to 35° C. The resulting thin slurry is redissolved via the addition of methanol (3.0 L). Glacial acetic acid (1.92 L, 33.5 moles) is again added portionwise to the batch over one to two hours, maintaining the temperature at 25° to 35° C. Toluene (613.5 kgW) combined with 5 ppm of an antistatic additive is prepared and adjusted to 20° to 25° C. in a separate vessel. Alternatively, a commercially available solution of toluene containing an antistatic additive may be used. (The antistatic additive is used solely for safety reasons.) The reaction mixture is added to the toluene with antistatic additive over approximately 15 minutes at 20° to 25° C. with maximum agitation. The reactor is rinsed with a methanol/toluene mixture, followed by a toluene rinse. The resulting slurry is stirred for three hours at 20° to 25° C., then it is filtered, and the filter cake is washed with toluene. The filter is blown with warm nitrogen for approximately five hours. The wet product cake is dried in an air oven at 45° to 50° C. to remove the toluene. Approximately 22–27 kgW of the "salt cake" (i.e., potassium-$d_4$T and inorganic salts) are obtained. Optionally, the wet cake can be used directly in the next step. The "salt cake" (44.4 kgW*) is dissolved in water (40 L) at approximately 25° C. and stirred for 45 minutes. The solution pH is lowered to 10.2 to 10.3 via the slow addition of 6N hydrochloric acid. The resulting slurry is further adjusted to pH 6.9 to 7.1 in the same manner. The slurry is cooled to 0° to 5° C. and held at this temperature range for approximately three hours. The product slurry is filtered and washed with cold water, followed by a cold isopropanol wash. The wet product cake is dried in an air oven at 45°–50° C. until the LOD is <1%. The dry product yield is 21–22.5 kgW of $d_4$T Primary, which represents 70–75% of theory.

*This step of Stage III may be performed with combined quantities of "salt cakes" produced from several runs.

Stage IV—Conversion of $d_4$T Primary to $d_4$-T-FP $d_4$T Primary (10.0 kgW, 44.6 moles) is dissolved in refluxing isopropanol (150 L) in the presence of activated charcoal (1.0 kgW) and diatomaceous earth (2.0 kgW). The mixture is held at reflux for approximately 20 minutes, then cooled to 75° to 80° C. The carbon slurry is filtered, and the filtration system is rinsed with hot isopropanol. The filtrate and wash solution are concentrated via atmospheric distillation to ensure sufficient room for the second portion of solution that will be added (see preparation of second portion in the next step). Meanwhile, additional $d_4$T Primary (5.0 kgW) is dissolved in refluxing isopropanol (75 L) in the presence of activated charcoal (0.5 kgW) and diatomaceous earth (2.0 kgW). Following the reflux, the slurry is filtered. The filtration system is rinsed with hot isopropanol, and the filtrate and rinse are combined with the concentrated filtrate and wash solution prepared previously (see above description). The distillation is continued until the concentrate reaches 40 to 50% of the combined dissolution volumes. The stirred concentrate is cooled to 0° to 5° C. for approximately two hours. The resulting slurry is held at 0° to 5° C. for approximately 2 hours, then it is filtered, and the product cake is washed with cold isopropanol. The cake is dried under vacuum at 45° to 50° C. to <0.5% LOD, and then the dried cake is milled. The yield of $d_4$T FP (finished new drug substance) is 12.8–13.5 kgW (i.e., 85–90% of theory).

The $d_4$T obtained is usually recrystallized from hot organic solvent solution as the final step in the process to produce $d_4$T of high purity. During the course of process development and scale-up, several recrystallization schemes were investigated. Initially, the pilot-plant recrystallization process involved cooling of hot isopropanol solution from 75°–82° C. to 65°–75° C. over 1 hour, and then to 0°–5° C. over 1.5 hours. This procedure yielded Form II, or mixtures of Forms I and II, which was not desirable.

Laboratory crystallization experiments showed that solutions of $d_4$T in isopropanol, if cooled rapidly, produced Form II or mixtures of I and II. Solubility studies showed that the crystallization temperature was critical to the solid-state formation. Above ambient temperature, the solubility difference in isopropanol increases, with Form I being less soluble. Using this finding, it was unexpectedly found that slow cooling of the hot isopropanol solution was found in the laboratory to reproducibly yield Form I, especially when Form I seed crystals were added to initiate crystallization. Consequently, the cooling temperature/time profile was modified such that the isopropanol solution is cooled to 65°–75° C. over 30 minutes to 1 hour, then further to 40°–45° C. over 2 to 3 hours, then rapidly to −5° C. to 5° C. The modified recrystallization process consistently results in the formation of Form I, devoid of Forms II and III.

It was further found that, although not critical, it is preferred to add seed crystals of Form I to the hot dissolved solution containing a mixture of one or more of Forms I, II and III to further enhance the yield of Form I obtained by the controlled recrystallization process herein described.

Continuous stirring during the cooling step is also critical, especially at temperatures above about 40° C., to ensure formation of Form I crystals. Stirring promotes the uniform distribution of the materials in the solution and prevents the formation of any of Forms II or III.

The solvent used for dissolving the $d_4$T mixture containing one or more of Forms I–III is critical. Organic solvents such as lower alkyl alcohols, including methanol, ethanol, n-propanol and isopropanol, and other solvents such as acetonitrile and ethyl acetate can be used. However, n-amyl alcohol and n-butyl alcohol (having a similar boiling point to n-amyl alcohol of about 118° C.) will not result in Form I formation using the process herein disclosed.

The temperature at which dissolution of the $d_4$T mixture of one or more of Forms I, II and III takes place to form a saturated solution of the $d_4$T in a particular solvent should be at least about 65° C. It is critical to start the procedure of recrystallization by controlled cooling at the initial temperature that a saturated solution is formed which is at least 65° C. to obtain adequate yields of Form I. If the controlled cooling step is started below this temperature, for example at 60° C. or less, crystals of both Forms I and II may result. Also, lower yields of Form I will be recovered from the $d_4$T mixture due to lower solubility levels of $d_4T$. Although saturated solution temperatures in excess of 80° C. can be used to dissolve $d_4T$ mixtures, it is generally preferable to dissolve at a saturated solution temperature range of about 70°–75° C., since $d_4T$ degradation products may begin to occur at elevated temperatures. In some cases the practical upper limit of saturated solution temperature may be necessitated by the boiling point of the solvent used (e.g. isopropanol boiling point of 82° C.; methyl alcohol boiling point of 65° C.).

The controlled cooling of the solution of $d_4T$ containing one or more of Forms I–III should be from a saturated solution temperature of at least 65° C. to obtain adequate yields of Form I crystalline $d_4T$. Cooling rates during recrystallization exceeding 20° C. per hour result in mixtures of the $d_4T$ polymorphic forms. Therefore, particularly for cooling from the saturated solution temperature down to about 40° C., it has been found the cooling rate should not exceed 20° C. per hour. More preferably, the cooling rate should be 10° C. in 15 minutes, followed by holding the solution at the resulting temperature for about one hour, repeating this procedure to about 40° C., and further cooling until the precipitation of substantially pure $d_4T$ crystalline Form I is substantially complete, and then recovering the same. It is understood that the cooling rate of 10° C. in 15 minutes, with a one hour hold of the resulting solution temperature, results in an effective cooling rate of 10° C. in one hour and 15 minutes, which does not exceed the maximum cooling rate of 20° C. per hour.

After dissolving the mixture containing one or more of Forms I–III to form a saturated solution, it is critical to control the cooling of the solution as above-mentioned until a temperature of about 40° C. is reached. Also, below temperatures of about 40°–45° C., the cooling rate need not be controlled, and can indeed be accomplished more rapidly than cooling between the initial saturated solution temperature and about 40° C. Such cooling below about 40° C. can continue down to a temperature of −5° to 5° C. to ensure complete recovery of the crystalline $d_4T$ Form I from the solution.

It is also critical that during the dissolving and cooling/recrystallization steps, anhydrous conditions be maintained to ensure that no Form III is contained in the final $d_4T$ product. Studies have shown that Form II can be obtained by the recrystallization of Form III in 100% isopropanol. However, moisture (i.e. $H_2O$ content) as low as 1% in the solution may yield a mixture of Forms II and III in the final product. In contrast to Forms II and III, suspensions of Form I are thermodynamically stable and do not show conversion to another form in any proportion of water/isopropanol mixtures studied.

The following examples are offered in order to more fully illustrate the present invention and should not be construed to limit the scope of the invention.

EXAMPLE 1

Conversion of Pilot Plant Lots of $d_4T$ to Pure Form I

Pilot Plant Lots 1–4 of dry anhydrous powdered $d_4T$ were made according to the procedure in Scheme A previously described. Representative samples of $d_4T$ from Lot 1 (i.e. Lots 1(a)–(d)) containing 300 mg. of $d_4T$ dissolved in 3 ml. of isopropanol contained in a 20 cc vial were prepared by adding the $d_4T$ material to isopropanol at 70° C. (maintained by a constant temperature water bath) until there was some visible undissolved solid. The resulting suspension was then filtered hot through S & S analytical filter papers (#604). The filtrate was then seeded with crystals of pure $d_4T$ Form I. The solutions in each vial were either stirred with a magnetic stir bar or left unstirred as the cooling was performed on each vial submerged in a water bath at different rates, as shown in Table 3. The controlled cooling was performed until the suspension reached a temperature of 30° C. The solid was then filtered through S & S analytical filter papers (#604) and air dried overnight at ambient temperature. This procedure was repeated for representative samples from Lot 2 (i.e. Lots 2(a)–(d)), Lot 3 (i.e. Lots 3(a)–(d)) and Lot 4. For Lot 4, no slow controlled cooling was employed. Powdered X-ray diffraction analysis on the initial Lots 1–4 samples and the final solid products obtained after the recrystallization was used to identify the presence or absence of Form I or II as shown in Table 3. In the initial lot samples, "minor amount" indicates less than about 5% of Form II in the sample. In the final $d_4T$ product after recrystallization, "unidentified" indicates some unidentified impurity (which is not Form I, II or III) resulting from the recrystallization process.

TABLE 3

Effect of Stirring and Rate of Cooling on Various Lots of $d_4T$ During Recrystallization From Isopropanol

| LOT# | CONDITIONS | INITIAL $d_4T$ PRODUCT | FINAL $d_4T$ Product |
|---|---|---|---|
| 1 (a) | w/stirring; 10° C./30 min. | I & II (minor amount) | I & unidentified |
| 1 (b) | w/stirring; 5° C./30 min. | I & II (minor amount) | I |
| 1 (c) | w/o stirring; 5° C./30 min. | I & II (minor amount) | I & II |
| 1 (d) | w/stirring; 10° C./15 min. (held for 1 hr. after each 10° C. drop) | I & II (minor amount) | I |
| 2 (a) | w/stirring; 10° C./30 min. | I & II (minor amount) | I |
| 2 (b) | w/stirring; 5° C./30 min. | I & II (minor amount) | I |
| 2 (c) | w/o stirring; 5° C./30 min. | I & II (minor amount) | I & II |

TABLE 3-continued

Effect of Stirring and Rate of Cooling on Various Lots of
$d_4T$ During Recrystallization From Isopropanol

| LOT# | CONDITIONS | INITIAL $d_4T$ PRODUCT | FINAL $d_4T$ Product |
| --- | --- | --- | --- |
| 2 (d) | w/stirring; 10° C./15 min. (held for 1 hr. after each 10° C. drop) | I & II (minor amount) | I |
| 3 (a) | w/stirring; 5° C./30 min. | I & II | I & unidentified |
| 3 (b) | w/o stirring; 5° C./30 min. | I & II | I, II & unidentified |
| 3 (c) | w/o stirring; very rapid cooling | I & II | II & unidentified |
| 3 (d) | w/stirring; 10° C./15 min. (held for 1 hr. after each 10° C. drop) | I & II | I |
| 4 | w/o stirring; very rapid cooling | I & II (minor amount) | I, II & unidentified |

As shown in Table 3 all lots during recrystallization, if left unstirred, resulted in a mixture of I and II. However, when the solution was stirred with slow cooling, pure Form I could be obtained. For example, a solution of Lot 3(c) when cooled very rapidly, gave mostly Form II. However, when a solution of Lot 2(a) is slowly cooled at the rate of 10° C./30 minutes, pure Form I is obtained. When a solution of Lot 1(a) was cooled at the rate of 10° C./30 minutes, the X-ray pattern indicated the presence of Form I and some other unidentified component. Cooling at a slower rate (5° C./30 minutes) or cooling at 10° C./15 minutes with one hour hold at the temperature after each temperature drop, gave the X-ray pattern of pure Form I, for Lots 1(b) and 1(d), respectively.

The effect of using various organic solvents during the slow cooling recrystallization step (b) in the process is illustrated in Example 2.

EXAMPLE 2

Add 500 mg. of a mixture containing $d_4T$ polymorphic Forms I and II to 5 ml. of each below-described organic solvent in a 20 cc round bottom flask maintained in a constant temperature water bath of 70°–75° C., until there is some visible undissolved solid in the flask. Filter the hot suspension through S & S analytical filter papers. Seed the filtrate with crystals of pure Form I. Cool each flask at the rate of 10° C./15 minutes with a 1 hour hold at that temperature after each cooling. Stir the solution in each flask with a magnetic stir bar while cooling. Continue the cooling until the suspension reaches ambient temperature. Filter the resulting precipitate through S & S analytical filter paper and allow to air dry overnight. Submit samples for analysis by X-ray powder diffraction.

The following results were obtained:

| Solvent | Polymorphic Form Isolated (As Determined by X-Ray Powder Diffraction Analysis |
| --- | --- |
| Ethanol | Form I |
| Acetonitrile | Form I |
| Ethyl acetate | Form I |
| n-Amyl alcohol | Form II |

What is claimed:

1. A process for preparing $d_4T$ polymorphic Form I from a mixture containing one or more of $d_4T$ polymorphic Forms I, II and III which comprises:

(a) dissolving the mixture under anhydrous conditions in an organic solvent: to form a saturated solution at a temperature of at least about 65° C., wherein said solvent is selected from the group consisting of methanol, ethanol, n-propanol, isopropanol, acetonitrile and ethyl acetate;

(b) continuously stirring while cooling the solution until the precipitation of substantially pure crystalline $d_4T$ polymorphic Form I is substantially complete, provided the cooling rate does not exceed about 20° C. per hour until a solution temperature of about 40° C. is reached, and (c) recovering substantially pure crystalline $d_4T$ polymorphic Form I.

2. The process of claim I wherein step (a) further comprises adding seed crystal of $d_4T$ polymorphic Form I to the solution.

3. The process of claim 2 wherein the solvent is isopropanol.

4. The process of claim 3 wherein the cooling in step (b) comprises reducing the solution temperature about 10° C. in 15 minutes, holding the solution at the resulting temperature for about one hour, repeating this procedure until a solution temperature of about 40° C. is reached, and further reducing the solution temperature until the precipitation of substantially pure crystalline $d_4T$ polymorphic Form I is substantially complete.

5. The process of claim 4 wherein the cooling in step (b) comprises reducing the solution temperature from 75°–82° C. to 65°–75° C. in about 30 minutes to one hour, further reducing the temperature to about 40°–45° C. during an additional 2 to 3 hours, and then rapidly reducing the temperature to about −5° C. to 5° C.

* * * * *